United States Patent [19]

Norton

[11] Patent Number: 4,773,901
[45] Date of Patent: Sep. 27, 1988

[54] CATHETER WITH SELECTIVELY RIGIDIFIED PORTION

[75] Inventor: William J. Norton, Berkeley Heights, N.J.

[73] Assignee: C. R. Bard, Inc., Murray Hill, N.J.

[21] Appl. No.: 581,533

[22] Filed: Feb. 21, 1984

Related U.S. Application Data

[63] Continuation of Ser. No. 336,290, Dec. 31, 1981, abandoned.

[51] Int. Cl.⁴ ............................................. A61M 25/00
[52] U.S. Cl. .................................................. 604/265
[58] Field of Search ............... 604/265, 264, 103, 280; 427/44

[56] References Cited

U.S. PATENT DOCUMENTS

| | | | |
|---|---|---|---|
| 3,566,874 | 3/1971 | Shephard et al. | 472/44 X |
| 3,695,921 | 10/1972 | Sheplard et al. | 427/2 |
| 3,736,939 | 6/1973 | Taylor | 604/265 |
| 4,306,563 | 12/1981 | Iwatshenko | 604/265 |

Primary Examiner—Stephen C. Pellegrino
Attorney, Agent, or Firm—Dennison, Meserole, Pollack & Scheiner

[57] ABSTRACT

A catheter having a relatively soft body formed of a hydrophobic elastomer and a tip portion coated with a water insoluble hydrophilic polymer grafted thereto to impart, in the dry state, rigidity to the tip portion. In use the hydrophilic coating absorbs or adsorbs water with resultant softening of the coating so as to render the tip portion soft. A method of facilitating placement of a catheter utilizing a transitorily rigidified tip portion is taught.

7 Claims, 1 Drawing Sheet

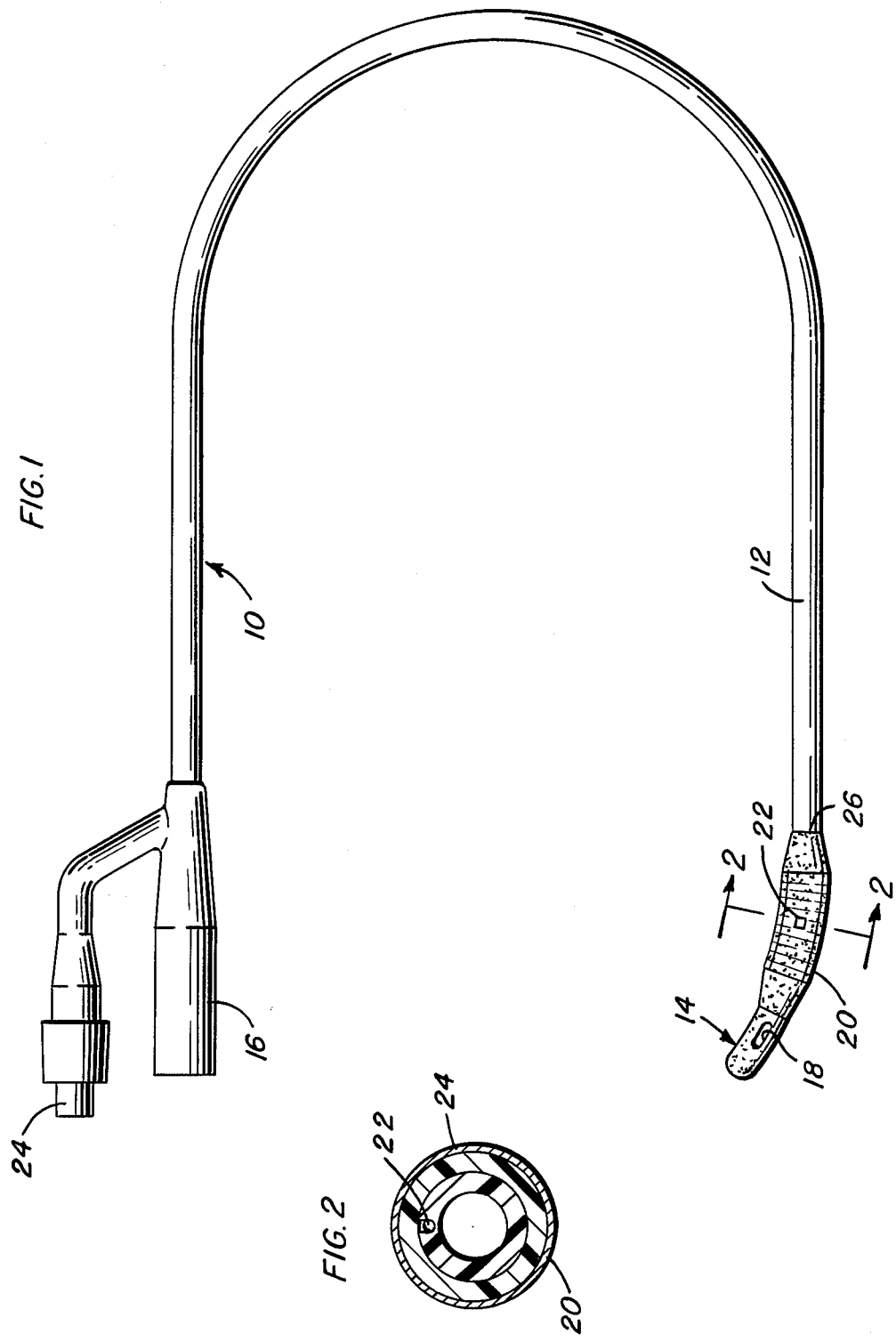

CATHETER WITH SELECTIVELY RIGIDIFIED PORTION

This application is a continuation, of application Ser. No. 336,290, filed 12/31/81 now abandoned.

BACKGROUND OF THE INVENTION

The present invention relates generally to provision of elastomeric tubing having utility for medical devices and particularly urethral and venous catheters. Such catheters normally are considered to be indwelling catheters in that they are placed and retained within the urethra or a vein for an extended period of time. Since the catheters in use comprise a foreign body they tend to cause considerable irritation of the tissue with which they come in contact.

The problem attendant minimizing irritation of tissue arising from an indwelling catheter is aggravated by the fact that it is generally preferable to provide a relatively rigid tip for the indwelling portion to facilitate passage of the catheter through the urethra or vein. It will be appreciated that the relatively rigid tip portion of the indwelling catheter only enhances the irritation of the adjacent tissue, i.e., bladder wall or inner wall of the vein. Thus, the invention herein resides in the provision of catheters constructed so as to have a tip portion that is relatively rigid so as to facilitate placement of the catheter, which relatively rigid tip portion in use becomes relatively less rigid whereby irritation of adjacent tissue is minimized.

A specific example of an instance where it is desirable to have different physical properties in various sections of a catheter is with respect to a urethral catheter wherein a relatively rigid curved tip is desirable to assist in the insertion of the catheter through the urethra which is curved and restrictive in the upper section.

In U.S. Pat. No. 3,865,666 to Shoney it is recognized that from a structural point of view a catheter, such as a urinary catheter, must be sufficiently rigid to ensure that as it traverses the urinary tract for placement in the bladder the catheter tube will not bend to an extent which results in occluding or reducing the size of the drainage lumen and the inflation lumen utilized to expand a balloon to retain the tip of the catheter within the bladder. While Shoney describes a catheter having a relatively rigid tip portion a significant problem arises by virtue of the fact that the tip portion maintains its rigidity in use thus leading to potential irritation of the bladder wall.

Catheters of the utility discussed herein are generally formed of silicone polymers which due to the hydrophobic characteristic of the silicone may then be provided with a hydrophilic coating derived from N-vinyl pyrrolidone (NVP) or acrylate and methacrylate monomers.

U.S. Pat. No. 4,055,682 to Merrill is directed to a catheter having a silicone body portion rendered hydrophylic by contacting it with NVP and exposing the catheter and NVP to ionizing radiation at high dosage rates. The hydrophilic polymeric layer of Merrill is so thin that the stiffness of the catheter after deposition of the polymeric layer, when dry, is not substantially greater than that of an uncoated catheter of the dame composition and degree of crosslinking.

U.S. Pat. Nos. 3,566,874 and 3,695,921 to Shepherd et al are representative of indwelling Foley urethral catheters made of natural or synthetic rubber and having an external coating of a hydrophilic acrylate or methacrylate polymer grafted thereto for the stated purpose of reducing irritation and infection considered to normally accompany the use of catheters. However, it has been found that problems are encountered in use when substantially the entire outer surface of the catheter within the urethra or vein is coated with a hydrophilic polymer since as discussed in U.S. Pat. No. 3,566,874 the resultant hydrophilic layers are stiff when dry.

SUMMARY AND OBJECTS OF THE INVENTION

In normal use of the conventional urethral and veinous catheters irritation of adjacent tissue by a relatively rigid catheter is of major concern. The present invention provides a catheter tip structure that is relatively rigid for purposes of placement of the catheter and which subsequent to placement in the body is rendered less rigid so as to minimize irritation of adjacent tissue.

The invention contemplates rendering the tip portion of urethral and veinous catheters formed of relatively flexible natural rubber or synthetic rubber, e.g. silicone rubber relatively rigid by the application; e.g., by grafting, to such tip portion a hydrophilic coating such as exemplified by the referenced patents to Merrill and Shepherd et al, which coatings render the tip portion relatively rigid. The disclosure of U.S. Pat. No. 3,695,921 to Shepherd et al is hereby incorporated by reference with respect to the provision of hydrophilic acrylate and methacrylate coatings that are rigid or stiff when dry. The disclosure of U.S. Pat. No. 4,055,682 to Merrill is hereby incorporated by reference primarily for the disclosure therein with respect to catheters having stiffness imparted thereto by use of a high dose of ionizing radiation, e.g., dose to which portion 36 is subjected, albeit the disclosure of Merrill is primarily directed to the grafting of NVP to a silicone catheter body so that the stiffness of the catheter after coating, when dry, is not substantially greater than that of an uncoated catheter of the same composition and degree of crosslinking.

The object of the invention comprising minimizing irritation of tissue adjacent the tip of the catheter is achieved by the hydrophilic nature of the "rigidfying" coating absorbing or adsorbing water and thereby becoming less rigid.

Various other objects and advantages of the invention will be readily apparent from the following detailed description taken in conjunction with the drawings in which an exemplary embodiment of the invention is shown.

DESCRIPTION OF THE DRAWINGS

FIG. 1 is a perspective view of an urethral catheter embodying the invention; and FIG. 2 is an enlarged cross-section of the tip portion of the catheter taken along the lines 2—2 of FIG. 1.

DESCRIPTION OF THE PREFERRED EMBODIMENT

Referring more specifically to FIGS. 1 and 2 of the drawings, there is provided an improved conventional constant drainage bag indwelling Foley urethral catheter 10 made of silicone rubber. The catheter 10 includes a tubular body portion 12 terminating in a tip portion indicated generally at 14. The catheter body 10 includes a drainage lumen, not shown, that connects a funnel 16 with a drainage port 18. An inflatable retaining bag or balloon 20 encompasses the tube 12, at a point inwardly of drainage port 18, and is sealed or otherwise connected thereto in conventional fashion. A longitudinally extending inflation lumen, not shown, terminates in an inflation port 22 which communicates the interior of the balloon 20 with a valve end portion or arm 24 for the introduction of air to inflate the balloon 20 to retain the catheter tip 14 in the bladder.

The body portion 12 is formed of a relatively flexible elastomer, e.g., silicone rubber, which is hydrophobic and generally inert with respect to physiological fluids it contacts. To facilitate passage of the relatively flexible catheter 10 through the urethra the tip portion 14 is rendered relatively rigid by provision of a rigidifying polymeric coating 24 which is applied, in the exemplary embodiment shown, such as from point 26 at the base of the balloon 20 to the end of the tip portion 14. It is essential to the present invention that the polymeric coating 24 be relatively rigid in a dry state, generally insoluble in physiological liquids, hydrophilic, and relatively flexible when wetted by physiological liquids such as urine and blood. The coating 24 thus may comprise a hydrophilic polymer such as formed from NVP or an acrylate or methacrylate monomer as set forth in the incoproated Merrill and Shepherd et al patents. It will be understood that hydrophilic polymers formed from NVP or acrylate and methacrylate monomers are merely exemplary and that other hydrophilic polymers are satisfactory as long as they impart sufficient rigidity, in a dry state, to the catheter tip portion 14 and are capable of softening in use, within a reasonable time, by absorption of a physiological fluid.

It will thus be appreciated that the hydrophilic coating 24 comprises means for rendering the catheter tip portion 14 relatively rigid to facilitate placement and wherein upon indwelling placement in the bladder the tip portion 14 is rendered relatively flexible so as to minimize irritation of the bladder wall.

It will be apparent that other variations may be perceived by those skilled in the art without departing from the scope of my invention as defined in the appended claims.

I claim:

1. A catheter comprising an elongated relatively flexible body portion formed of a hydrophobic polymer and including a reversibly rigidified tip portion of minor longitudinal extent, said top portion only including a physiological fluid-insoluble hydrophilic non-hydrated polymeric coating for rendering the top portion relatively rigid in a dry state, said coating being relatively flexible when hydrated by a physiological fluid.

2. The catheter of claim 1 wherein the tip portion is arcuate.

3. The catheter of claim 1 comprising a Foley catheter.

4. The catheter of claim 1 comprising a venous catheter.

5. The catheter of claim 1 wherein said means comprises a hydrophilic polymeric coating formed from a monomer selected from the group comprising N-vinyl pyrrolidone, acrylate and methacrylate.

6. A method of reversibly rigidifying a predetermined minor tip portions of the length of an elongated relatively flexible catheter formed of a hydrophobic polymer to facilitate insertion of the catheter into a body cavity, comprising externally coating only the tip portion with a rigidifying physiological fluid-insoluble hydrophilic non-hydrated polymer which is relatively flexible when hydrated by the aqueous moiety of a physiological fluid.

7. The catheter of claim 6 wherein said coating comprises a hydrophilic polymeric coating formed from a monomer selected from the group comprising N-vinyl pyrrolidone, acrylate and methacrylate.

* * * * *